United States Patent
Brattström

(10) Patent No.: US 8,637,099 B2
(45) Date of Patent: Jan. 28, 2014

(54) USE OF VITEX AGNUS CASTUS EXTRACTS FOR PREPARING A MEDICAMENT

(75) Inventor: Axel Brattström, Magdeburg (DE)

(73) Assignee: Max Zeller Sohne AG, Romanshorn (CH)

(*) Notice: Subject to any disclaimer, the term of this patent is extended or adjusted under 35 U.S.C. 154(b) by 291 days.

(21) Appl. No.: 12/733,171

(22) PCT Filed: Aug. 28, 2008

(86) PCT No.: PCT/EP2008/007051
§ 371 (c)(1),
(2), (4) Date: Feb. 16, 2010

(87) PCT Pub. No.: WO2009/027086
PCT Pub. Date: Mar. 5, 2009

(65) Prior Publication Data
US 2010/0151059 A1    Jun. 17, 2010

(30) Foreign Application Priority Data
Aug. 29, 2007    (EP) .................................... 07016897

(51) Int. Cl.
*A61K 36/00* (2006.01)
(52) U.S. Cl.
USPC .......................................... 424/778; 424/725
(58) Field of Classification Search
None
See application file for complete search history.

(56) References Cited

U.S. PATENT DOCUMENTS 6,727,363 B2 *   4/2004   Tomasi et al. .................... 546/69

FOREIGN PATENT DOCUMENTS

DE            4305452 A1  *  8/1994

OTHER PUBLICATIONS

Shellenberg. Treatment for the premenstrual syndrome with angus castus fruit extract: prospective, randomised, placebo controlled study. BMJ. vol. 322. Jan. 20, 2001. pp. 134-137.*
Brattstrom, A., et al.: "CNS Dopamine Agonistic Action of the Vitex Agnus Castus Extract Ze 440 in Freely Moving, Chronically Instrumented Animals" Planta Medica, Thieme, Stuttgart, DE, vol. 73, No. 9, Aug. 1, 2007, p. 814 (Abstract Only).
Nasri, Sima, et al.; "The Effects of Vitex Agnus Castus Extract and its Interaction with Dopaminergic System on LH and Testosterone in Male Mice" Pakistan Journal of Biological Sciences; Jul. 15, 2007, vol. 10 No. 14 (Abstract Only).
Meier, B., et al.; "Pharmacological Activities of Vitex Agnus-Castus Extracts in Vitro"Phytomedicine: International Journal of Phytotherapy and Phytopharmacology; Oct. 2000, vol. 7, No. 5 (Abstract Only).
Jarry, Hubertus, et al.; "In Vitro Assays for Bioactivity-guided Isolation of Endocrine Active Compounds in Vitex Agnus-Castus "Maturitas, vol. 55 No. Suppl. 1, Nov. 2006 (Abstract Only).

* cited by examiner

*Primary Examiner* — Chris R Tate
*Assistant Examiner* — Deborah Davis
(74) *Attorney, Agent, or Firm* — Nath, Goldberg & Meyer; Tanya E. Harkins

(57) ABSTRACT

The present invention relates to the use of fruit extract from *Vitex agnus castus* and/or one or more isolated and/or synthetically prepared bicylic diterpenes from *Vitex agnus castus* for the preparation of a medicament for the treatment of movement disorders. In particular, the invention is directed to the preparation of medicaments for treating Parkinson disease (PD), Periodic Limb Movement disorder (PLMD) and Restless Leg Syndrome (RLS), Huntington disease (HD) and Essential Tremor (ET), preferably familiar ET. Furthermore, the invention concerns a pharmaceutical composition comprising a fruit extract from *Vitex agnus castus* and/or one or more isolated and/or synthetically prepared bicylic diterpenes from *Vitex agnus castus* and at least one pharmaceutically compatible dopamine D2 and/or D3 receptor agonist.

14 Claims, 9 Drawing Sheets

USE OF VITEX AGNUS CASTUS EXTRACTS FOR PREPARING A MEDICAMENT

This is a U.S. national phase Application filed under 35 U.S.C. 371 of PCT/EP2008/007051 A2, filed 28 Aug., 2008 claiming priority benefit from EP Application No. 07016897.6, filed 29 Aug. 2007, the entire content of which is hereby incorporated by reference.

The present invention relates to the use of fruit extract from *Vitex agnus castus* and/or one or more isolated and/or synthetically prepared bicylic diterpenes from *Vitex agnus castus* for the preparation of a medicament for the treatment of movement disorders. In particular, the invention is directed to the preparation of medicaments for treating Parkinson disease (PD), Periodic Limb Movement disorder (PLMD) and Restless Leg Syndrome (RLS), Huntington disease (HD) and Essential Tremor (ET). Furthermore, the invention concerns a pharmaceutical composition comprising a fruit extract from *Vitex agnus castus* and/or one or more isolated and/or synthetically prepared bicylic diterpenes from *Vitex agnus castus* and at least one pharmaceutically compatible dopamine D2 and/or D3 receptor agonist.

PRIOR ART

The term movement disorder encompasses a number of disorders like Parkinson disease (PD), Periodic Limb Movement disorder (PLMD), Restless Leg Syndrome (RLS), Huntington disease (HD) and Essential Tremor (ET), in particular familiar ET. The above movement disorders have in common that the dopaminergic receptors D2 and/or D3 are involved in sensimotory dysfunctions.

Parkinson disease (PD) is an age-related movement disorder affecting about 2% of the population over the age of 65 years. It is characterized by bradykinesia, rigidity, resting tremor and postural instability. The neuropathologic hallmarks of PD are the loss of dopaminergic neurons in the substantia nigra and the presence of intraneural cytoplasmic inclusions known as Lewy bodies. The clinical manifestations of PD are primarily the consequence of progressive and selective degeneration of dopaminergic neurons in the pars compacta of the substantia nigra that give rise to the nigrostriatal pathway. Disappearance of this tract provokes a depletion of dopamine in the striatum, where it is required for normal motor (and cognitive) function. Correspondingly, PD has long been treated by the administration of the dopamine precursor agonist L-Dopa. However, L-Dopa is suspected of exerting neurotoxic properties that can accelerate the loss of dopaminergic neurons. Furthermore, the pharmacokinetic profile of L-Dopa is highly variable, leading to abrupt transitions of active and passive phases. It elicits marked dyskinesia and its therapeutic efficacy gradually wanes over years of exposure.

In recent years pramipexol (Mirapexin®, Sifrol®, Mirapex®) and repinirole (Requio®) were introduced for relieving motor deficits in PD and both demonstrated a slowing in the loss of dopaminergic terminals upon long-term administration to PD patients. Unlike most common dopamine receptor agonists both have a high affinity to the D3 receptor subtype. In the past it has often mistakenly been assumed that D2 receptors are the major subtype involved in PD. This assertion neglects the fact that both pramipexol and ropinirole have a much higher affinity for D3 receptors than D2 receptors, and ignores a substantial body of data indicating, to the contrary, that D3 receptors are primarily involved in the neuroprotective actions of dopaminergic agonists in PD. Both D3 receptor agonists demonstrate neuroprotection, neurorestauration as well as regeneration of dopaminergic pathways. The D3 receptor is known to play an important role in dopaminergic development. Furthermore, pharmacological activation of the D3 receptor has been shown to trigger neurogenesis in the substantia nigra of adult brain by cell proliferation in the substantia nigra pars compacta with a time-dependent adoption of a neuronal dopaminergic phenotype. In a rodent model of PD it was demonstrated that D3 receptor regeneration coincides with a substantial and persistent recovery of locomotor function. For a review on PD and dopamine receptor involvement see J. N. Joyce and M. J. Millan, *Dopamine D3 receptor agonists for protection and repair in Parkinson disease*, Current Opinion in Pharmacology, Neurosciences, vol. 7(1), February 2007, 100-105; Van Kampen and Eckman, *Dopamine $D_3$ receptor agonist delivery to a model of Parkinson's disease restores the nigrostriatal pathway and improves locomotor behavior*, The Journal of Neuroscience, 26(27), 2006: 7272-7280; Van Kampen & Robertson, *A possible role for dopamine D3 receptor stimulation in the induction of neurogenesis in the adult rat substantia nigra*, Neuroscience, 136, 2005: 381-386.

However, all dopamine agonists have a rather large number of serious adverse effects. For example, treatment with pramipexol may lead to side effects such as abnormal behaviour and dreams, confusion, constipation, dizziness, delusion, dyskinesia, fatigue, hallucinations, headache, hypotension, increased appetite, insomnia, libido problems, nausea, peripheral edema, somnolence, sudden falling asleep and weight gain. Similarly, patients treated with ropinole may suffer from confusion, hallucinations, delusion, paranoia, libido problems, somnolence, dyskineasia, dizziness, hypotension, nausea, abdominal pain, vomiting, dyspepsia and leg edema. Clearly, there is a need for dopamine receptor agonists for treating PD with less side effects that can either be administered alone or at least allow for reducing the dose of other dopaminergic agents.

The Restless Leg Syndrome (RLS) is one of the commonest neurological sensorimotor disorders at least in the western countries and is often associated with periodic limb movement disorder (Periodic Limb Movement disorder (PLMD) during sleep leading to severe insomnia. Clinically the legs are mostly affected but arm involvement has also been reported. Its underlying pathogenesis is presently unknown. Familiar predisposition, end-stage renal disease, pregnancy, iron deficiency, abuse and even PD have been implicated. The excellent response to dopaminergic drugs points to a central role of dopamine in the pathophysiology of RLS. Owing to the putative dopaminergic basis of RLS, a common pathophysiology with PD has been suggested. However, the interaction of dopamine, iron and probably other compounds to generate a circadian pattern in the occurrence of RLS and PLM symptomatology suggests a complex disorder that may result from a complex dysfunction of interacting neuronal networks at one or several levels of the CNS and involving numerous neurotransmitter systems. For a review on RLS/PLM and dopamine receptor involvement see Barriere et al., *The restless leg syndrome*, Progress in Neurobiology, 77 (2005), 139-165.

Today, the D2 and D3 receptor dopamine agonists pramizol and ropinirole have established their medical utility as a first choice for the treatment of RLS and PLMD. For further information in this respect, see Sven Happe, *Dopaminagonisten in der Behandlung des Restless-Legs-Syndroms*, Psychopharmakotherapie, 13. Jahrgang, Heft 5, 191-196 (2006); Partinen et al., *Efficacy and safety of pramipexole in idiopathic restless legs syndrome: A polysomnographic dose-finding study-The PRELUDE study*, Sleep Medicine, 7, 407-

417 (2006); K. Stiassny-Kolster and W. H. Oertel, *Low-dose pramipexole in the management of Restless Legs Syndrome*, Neuropsychobiology, 50:65-70 (2004); Cheere et al. *Ropinirole for the treatment of Restless Legs Syndrome*, Adis Drug Profile, Adis Int. Ltd, Auckland, New Zealand CNS Drugs 2004:18(11):747-754; Vignatelli et al., *EFNS guidelines on management of restless legs syndrome and periodic limb movement disorder in sleep*, European Journal of Neurology, 13:1049-1065 (2006). These double action (D2 and D3 receptor) agonists avoid the augmentation often encountered with L-Dopa and other D2 agonists and are also longer acting. However, these modern compounds still have the above mentioned drawbacks. Hence, there is a need in the art for efficient but at the same time more agreeable D2/D3 agonists for treating the movement disorders RLS and PMDS.

Huntington disease (HD) is a rare neurological disorder caused by a trinucleotide expansion in the Huntington gene resulting in neuronal cell death in selected areas of the brain including the substantia nigra and is a terminal illness. Its most obvious symptoms are abnormal body movements called chorea and a lack of coordination. Dopamine agonists are the common medication for controlling the chorea. Once again, the double action (D2 and D3 receptor) dopamine receptor agonist pramipexol has established its benefits in this movement disorder (Bonelli & Wenning, *Pharmacological management of Huntington's disease: an evidence-based review*, Curr. Pharm. Des. 12(21), 2006: 2701-20). However, it may result in aggravating bradykinesia or dystonia as well as other before mentioned adverse effects.

Essential tremor (ET), one of the most common neurological disorders, is characterized by kinetic or postural tremor, whereas the latter worsens with movement, for example, shaking of hands and sometimes other parts of the body including the head. ET is defined according to the clinical criteria proposed in the Consensus Statement on Tremor by the Movement Disorder Society. Many of its cases are associated with a gene mutation whereas others are idiopathic. A growing body of evidence suggests that this disorder is not monosymptomatic but heterogenous, as it is associated in some cases with PD, myclonus, dystonia, cerebellar dysfunction and other motor and sensory abnormalities. The Ser9Gly variant of the dopamine D3 receptor on chromosome 3q13 is associated with risk and age of onset of ET. Dopamine D3 receptor variants are considered a possible common mechanism partly responsible for the pathogenic events leading to ET and PD in phenotype or coexistence of ET and PD in some cases (Deng et al., *Genetics of essential tremor*, Brain, 130, 2007, 1456-1464; Jeanneteau et al., *A functional variant of the dopamine $D_3$ receptor is associated with risk and age-at-onset of essential tremor*, PNAS, 103 (28), 2006: 10753-10758).

In summary, D2 and/or D3 agonists of dopaminergic receptors have established themselves as the treatment of choice in movement disorders. However, their abundant and often harsh adverse effects lead to a lack of acceptance among patients and, hence, medical practitioners often revert to these drugs only in severe cases of movement disorders and attempt to dose them as low as possible.

The shrub Vitus agnus castus (VAC) has a long tradition as an herbal remedy and was used in ancient times not only as an anaphrodisiac and for preserving chastity but also for treating diverse disturbances of the female genital system. In actual clinical trials extracts of the fruits, Agni casti fructus, demonstrated a relieve of the premenstrual syndrome (PMS) and especially breast swelling and pain probably due to its dopaminergic effect. Today VAC extracts are available for treating PMS symptoms in a number of countries, e.g. Switzerland, extract Ze440 from Zeller AG, Herbal Medicinal Products, CH-8590 Romanshorn 1, brand names Prefemin® and Premens®, (Wuttke et al., *Chaste tree (Vitex agnus-castus)-pharmacology and clinical indications*, Phytomedicine, 10:348-57 (2003)).

Safety studies on VAC extracts indicate that the vast majority of adverse events reported were rather mild and transient, including nausea, headache, gastrointestinal disturbances, menstrual disorders, acne, pruitus and erythematous rash. Theoretically, VAC might interfere with oral contraceptives, hormone replacement therapy, sex hormones, and dopamine agonists or antagonists. However, evidence-based contraindications are yet unknown.

In in vitro studies pharmacological activities of these extracts have been attributed to opiate $\mu$ and dopamine D2 receptors. (Meier et al., *Pharmacological activities of Vitex agnus-castus extracts in vitro*. Phytomedicine 7:373-381 (2000)). These receptors are widely distributed in the body's periphery as well as in the brain. However, the extracts ability to enter the brain and affect neuronal communication is questionable.

The mechanism of action of VAC extracts was recently proposed to be dopaminergic and estrogenic in nature. Employing in vitro assays for bioactivity-guided isolation endocrine active compounds were identified as dopaminergic bicyclic diterpenes and the estrogenic flavonoids penduletin and apigenin, both of which are specific ligands for the estrogen $\beta$ receptor. Most of the isolated bicylic diterpenes had a labdane type skeleton, among them the most prominent being rotundifuran and 6$\beta$,7$\beta$-diacetoxy-13-hydroxy-labda-8,14-dien. The dopaminergic diterpene fractions demonstrated a specific D2 receptor ligand activity, the fraction with the highest dopaminergic activity being a mixture of diterpenes of the clerodane type, i.e. clerodanediol and clerodanetriol structures, both with a 3-hydroxy, 3-methyl-pent-4-enyl group, e.g. cleroda-7,14-dien-13-ol and cleroda-1,3,14-trien-13-ol (Hubertus Jarry et al., *In vitro assays for bioactivity-guided isolation of endocrine active compounds in Vitex agnus-castus*, ScienceDirect, Maturitas (2006), doi:10.1016/j.maturitas.2006.06.014).

It is an object of the present invention to provide new medical indications for extracts and pharmacologically active components of extracts of *Vitus agnus castus*.

In view of the prior art on movement disorders and dopamine agonist-related treatment, it is also an object of the present invention to provide pharmaceutical means for alleviating or even eliminating one or more symptoms of common movement disorders with less or even no adverse effects compared to current dopamine agonists.

In addition, it is an object of the present invention to provide pharmaceutical means suited to be administered to patients suffering from movement disorders together with dopamine receptor agonists such as, e.g. pramipexol and ropinirole, that will allow a reduction in the dosage of the dopamine receptor agonists, subsequently leading to reduced side effects but still efficient medical action.

DESCRIPTION OF THE INVENTION

It was surprisingly found that an extract from *Vitex agnus castus* can be used to treat movement disorders.

Hence, in a first aspect the present invention relates to the use of extract from *Vitex agnus castus* for the preparation of a medicament for the treatment of movement disorders.

The term "movement disorder" is well established in the art. It typically encompasses disorders involving clinically apparent abnormal motor activity due to pathophysiological changes in the brain of patients. In a preferred embodiment, the term "movement disorder" as used herein refers to disorders involving clinically apparent abnormal motor activity due to pathophysiological changes in the nigrostriatal pathway of patients. All movement disorders have in common that the dopaminergic system is somehow compromised in function, either due to loss of dopaminergic neurons, dopaminergic receptors or physiological dopaminergic agonists or due to a reduced release of the neurotransmitter dopamine and/or related agonists.

In all movement disorders the D2 and/or D3 dopamine receptor ligand systems have been identified as relevant disease factors.

In a preferred embodiment the present invention is directed to the preparation of medicaments for treating movement disorders that are responsive to D2 and/or D3 receptor agonists, more preferably to the preparation of medicaments for treating movement disorders that are responsive to D2 and D3 receptor agonists, most preferably to the preparation of medicaments for treating movement disorders that are responsive to D3 receptor agonists.

In a more preferred embodiment, the present invention is directed to medicaments for treating movement disorders selected from the group consisting of Parkinson disease (PD), Periodic Limb Movement disorder (PLMD), Restless Leg Syndrome (RLS), Huntington disease (HD) and Essential Tremor (ET), preferably familiar ET.

In a particularly preferred embodiment, the present invention is directed to medicaments for treating movement disorders selected from the group consisting of Parkinson disease (PD), Periodic Limb Movement disorder (PLMD) and Restless Leg Syndrome (RLS).

Most preferably, the movement disorder is Restless Leg Syndrome (RLS).

*Vitex agnus castus* (VAC), also known as chaste tree, is a shrub belonging to the genus *Vitex* of the Verbenaceae family that is widespread on riverbanks and on shores in the Mediterranean region as well as in Asia. Its berries resemble peppercorns, hard, with a purple to black skin, yellowish within, half-covered by their sage-green calyces and containing four seeds. The parts typically used today as herbal medicine are the dried ripe berries (Agni casti fructus). Most often aqueous-alcoholic extracts (50-70%), for example 60% aqueous ethanolic extracts, are prepared from the crushed fruits.

The extract for use in the present invention may be prepared with any suitable extraction means. Suitable extraction means for chaste tree fruits are well known in the art. In a preferred embodiment, the extraction means for preparing the extract for use in the present invention is a hydrophilic solvent such as water, ether, alcohol, preferably methyl, ethyl or propyl alcohol. In a more preferred embodiment, the solvent is an aqueous extract, preferably one comprising 40 to 80% alcohol, more preferably 50 to 70% alcohol, even more preferably about 60% alcohol, with aqueous ethanolic extracts being most preferred. In a preferred embodiment ripe fruits of VAC are extracted for preparing extracts for practicing the present invention.

In a preferred embodiment, the term "extract from *Vitex agnus castus*", as used herein, is meant to further encompass one or more isolated and/or synthetically prepared bicyclic diterpenes from VAC. In other words, the extracts for use in the present invention may be substituted by one or more isolated and/or synthetically prepared bicyclic diterpenes from VAC. Accordingly, the aspects and embodiments taught herein are understood to relate to the use of VAC extracts, the use of one or more isolated and/or synthetically prepared bicyclic diterpenes from VAC, or the use of mixtures of VAC extracts and one or more isolated and/or synthetically prepared bicylic diterpenes from VAC. Hence, when a specific embodiment herein reads on VAC extracts, the use of bicyclic terpene(s) and mixtures of VAC extracts and VAC terpenes is also disclosed.

Preferably, one or more of the isolated and/or synthetically prepared bicyclic VAC diterpenes have a labdane type structure, more preferably they are rotundifuran and/or 6β,7β-diacetoxy-13-hydroxy-labda-8,14-dien.

More preferably, one or more of the isolated and/or synthetically prepared VAC bicyclic diterpenes are of the clerodane type, i.e. clerodanediol and clerodanetriol structures, preferably both with a 3-hydroxy,3-methyl-pent-4-enyl group, most preferably cleroda-7,14-dien-13-ol and/or cleroda-1,3,14-trien-13-ol (for a review on these substances see Hubertus Jarry et al., *In vitro assays for bioactivity-guided isolation of endocrine active compounds in Vitex agnus-castus*, ScienceDirect, Maturitas (2006), doi:10.1016/j.maturitas.2006.06.014).

Most preferably, the isolated and/or synthetically prepared bicylic diterpenes are a mixture of diterpenes of the clerodane type, preferably a mixture with clerodanediol and clerodanetriol structures, more preferably both with a 3-hydroxy, 3-methyl-pent-4-enyl group, most preferably a mixture of cleroda-7,14-dien-13-ol and cleroda-1,3,14-trien-13-ol.

In a preferred embodiment of the invention, the content of extract of *Vitex agnus castus* in the medicament lies in the range of 1 to 100 mg, preferably 5 to 80 mg, more preferably 10 to 50, most preferably 20 to 40 mg extract per dosage form and optionally comprises at least one pharmaceutically compatible excipient. For the isolated and/or synthetically prepared bicyclic diterpenes from VAC, this dosage range can be adapted accordingly. Typically, about 2 to 4% by weight of the extract are bicyclic diterpenes.

It was surprisingly found that VAC extracts demonstrate their dopaminergic effects in the brain after oral administration, demonstrating their gastrointestinal stability and their ability to pass the blood-brain barrier.

In a preferred embodiment the extract and/or the above-mentioned bicyclic diterpene(s) for practicing the present invention is (are) formulated as a dosage form for oral, parenteral or transdermal administration, preferably for oral administration, more preferably as a solution or a tablet for oral administration.

For example, a tablet comprising 20 mg native extract (e.g. from an about 60% aqueous ethanolic VAC extract; a tablet as already registered in Switzerland) with a drug/extract ratio of approximately 6-12:1 corresponds to 120-240 mg dried drug. Solid dosage forms of VAC extracts for long term treatment with daily intake suitable for use in the present invention may be prepared as film-coated tablets by mixing the dry extract with the conventional excipients necessary for direct tableting and by compressing these on a rotary tableting machine. For small tablets special disintegrating agents are not required since small tablets disintegrate quickly. A suitable coating may be realized by a coater with hydroxypropylmethylcellulose pigmented with titanium oxide.

Medicaments resulting from the present invention have the advantage that they are mostly free of adverse events, i.e. they have rather few mild and transient effects, and that they exert an agonistic effect on the D2 and, in particular, on the D3 dopaminergic receptors in the brain of patients, thus, alleviating or even eliminating some or even all of the symptoms associated with movement disorders. In some severe cases of movement disorders the extracts might not be sufficient to completely alleviate symptoms. In these cases, the extracts for use in the present invention can still be of great value. For example, the extracts can be useful for combining with other dopamine agonists and will allow for reducing the dosage of the other agonists in order to reduce their adverse effects or avoid augmentation, as in the case of L-Dopa.

In a second aspect, the present invention relates to the before mentioned use of an extract of Vitus agnus castus and/or one or more isolated and/or synthetically prepared bicyclic diterpenes from Vitus agnus castus), wherein the medicament further comprises at least one pharmaceutically compatible dopamine D2 and/or D3 receptor agonist.

Preferably, the further dopamine D2 and/or D3 receptor agonist is selected from the group consisting of L-dopa, tramadol, paroxetine, metanicotine, piridebil, ropinirole, cabergoline, carbidopa, bromocryptine, domperidone, pergolide, α-dihydroergocryptine, pramipexol, rotigotine and apomorphine.

More preferably, the medicament further comprises at least one pharmaceutically compatible dopamine D2 and D3 receptor agonist, in particular one selected from the group consisting of pramipexol, piribedil, cabergoline and ropinirole, most preferably it is pramipexol.

In a third aspect, the present invention is directed to a pharmaceutical composition comprising a fruit extract from VAC and/or one or more isolated and/or synthetically prepared bicylic diterpenes from VAC in a pharmaceutically effective amount and at least one pharmaceutically compatible dopamine D2 and/or D3 receptor agonist and optionally at least one pharmaceutically compatible excipient or carrier.

Preferably, one or more of the isolated and/or synthetically prepared bicylic VAC diterpenes have a labdane type skeleton, more preferably they are rotundifuran and/or 6β,7β-diacetoxy-13-hydroxy-labda-8,14-dien.

More preferably, one or more of the isolated and/or synthetically prepared VAC bicylic diterpenes are of the clerodane type, i.e. clerodanediol and clerodanetriol structures, preferably both with a 3-hydroxy,3-methyl-pent-4-enyl group, most preferably cleroda-7,14-dien-13-ol and/or cleroda-1,3,14-trien-13-ol (for a review on these substances see Hubertus Jarry et al., *In vitro assays for bioactivity-guided isolation of endocrine active compounds in Vitex agnus-castus*, ScienceDirect, Maturitas (2006), doi:10.1016/j.maturitas.2006.06.014).

Most preferably, the isolated and/or synthetically prepared bicylic diterpenes are a mixture of diterpenes of the clerodane type, preferably a mixture comprising clerodanediol and clerodanetriol structures, more preferably both with a 3-hydroxy, 3-methyl-pent-4-enyl group, most preferably a mixture of cleroda-7,14-dien-13-ol and cleroda-1,3,14-trien-13-ol.

Suitable carriers and excipients are well-known in the art. A carrier or excipient can be a solid, semi-solid or liquid material which can serve as a vehicle or medium for the active ingredients. One of ordinary skill in the art in the field of preparing pharmaceutical compositions can readily select the proper form and mode of administration depending upon the particular characteristics of the product selected, the movement disorder to be treated, the stage of the movement disorder and other relevant circumstances (*Remington's Pharmaceutical Sciences*, Mack Publishing Co. (1990)). The proportion and nature of the pharmaceutically acceptable carrier or excipient are determined by the solubility and chemical properties of the active agent selected, the chosen route of administration and standard pharmaceutical practice. Preferably, the pharmaceutical preparation according to the present invention may be adapted for oral, parenteral or transdermal use and may be administered to the patient in the form of tablets, capsules, suppositories, solutions, suspensions, or the like.

In a preferred embodiment, the pharmaceutical composition of the invention comprises 5 to 80 mg, more preferably 10 to 50, most preferably 20 to 40 mg extract (and/or corresponding amounts of isolated or synthetically prepared VAC bicyclic diterpenes) per dosage form and 0.01 to 10 mg, preferably 0.1 to 1 mg, of at least one pharmaceutically compatible dopamine D2 and/or D3 receptor agonist and optionally comprises at least one pharmaceutically compatible excipient. More preferably, it is a solution or a tablet, most preferably a tablet.

In a preferred embodiment, the dopamine D2 and/or D3 receptor agonist for combination with the VAC extract/bicyclic diterpenes in the pharmaceutical composition of the invention is selected from the group consisting of L-dopa, tramadol, paroxetine, metanicotine, piridebil, ropinirole, cabergoline, carbidopa, bromocryptine, domperidone, pergolide, α-dihydroergocryptine, pramipexol, rotigotine and apomorphine.

More preferably, the at least one pharmaceutically compatible dopamine receptor agonist is a D2 and D3 receptor agonist, most preferably one selected from the group consisting of pramipexol, cabergoline, piribedil and ropinirole, preferably it is pramipexol.

In a fourth aspect, the present invention is directed to a method of treating a movement disorder, preferably a movement disorder that is responsive to D2 and/or D3 receptor agonists, more preferably a movement disorder selected from the group consisting of Parkinson disease (PD), Periodic Limb Movement disorder (PLMD), Restless Leg Syndrome (RLS), Huntington disease (HD) and Essential Tremor (ET), preferably familiar ET, in a mammal, which method comprises administering to the mammal a therapeutically effective amount of extract and/or isolated and/or synthetically prepared bicyclic diterpenes from *Vitex agnus castus* and optionally at least one pharmaceutically compatible dopamine D2 and/or D3 receptor agonist, whereupon the mammal is treated for a movement disorder.

The disclosures of all documents cited herein are hereby incorporated in their entireties by reference.

While this invention has been described with an emphasis upon preferred embodiments, it is understood and intended that the invention can be practiced otherwise than as specifically described in these embodiments. Accordingly, this invention includes all modifications encompassed within the spirit and scope of the invention as defined by the claims.

In the following the present invention will be illustrated in more detail by way of examples, which are not to be construed as limiting the scope of the appended claims.

FIGURES

FIG. 1 shows the time course of the effect of oral administration of saline on the change of spectral power in four brain areas. Frequency ranges of delta, theta, alpha1, alpha2, beta1 and beta2 power are given under the section "methods". Data are given as average of n=8 rats. Ordinate on the right depicts percent changes in ECG power activity with respect to pre-drug reference (100%).

FIG. 2 shows the time course of the effect of oral administration of 25 mg/kg of VAC extract on the change of spectral power in four brain areas. Frequency ranges of delta, theta, alpha1, alpha2, beta1 and beta2 power are given under the section "methods". Data are given as average of n=8 rats.

Ordinate on the right depicts percent changes in ECG power activity with respect to pre-drug reference (100%).

FIG. 3 shows the time course of the effect of intraperitoneal administration of 4 mg/kg of the dopamine D2 antagonist L 741,626 on the change of spectral power in four brain areas. Frequency ranges of delta, theta, alpha1, alpha2, beta1 and beta2 power are given under the section "methods". Data are given as average of n=7 rats. Ordinate on the right depicts percent changes in motion with respect to pre-drug reference (100%).

FIG. 4 shows the time course of the effect of oral administration of 25 mg/kg of VAC extract in the presence of the dopamine D2 antagonist L 741,626 (2 mg/kg i.p.) on the change of spectral power in four brain areas. Frequency ranges of delta, theta, alpha1, alpha2, beta1 and beta2 power are given under the section "methods". Data are given as average of n=8 rats. Ordinate on the right depicts percent changes in ECG power activity with respect to pre-drug reference (100%).

FIG. 5 shows the Interaction of VAC extract and the dopamine receptor blocker L741,626 during the second hour after administration. VAC extract was administered orally, L741,626 intraperitoneally. Frequency ranges of delta, theta, alpha1, alpha2, beta1 and beta2 power are given under the section "methods". Data are given as average of n=8 rats (65-125 min after oral administration). A time course for the effects on alpha2 frequencies within the frontal cortex and striatum is provided in FIG. 9 and FIG. 10.

FIG. 6 shows the time and dose dependency of the effect of oral administration of VAC extract on the change of alpha2 spectral power in the frontal cortex. Data are given as average of n=8 rats.

FIG. 7 Time and dose dependence of the effect of oral administration of *Vitex agnus-castus* extract on the change of alpha2 spectral power in the striatum. Data are given as average of n=8 rats.

FIG. 8 demonstrates the locomotor activity of rats in the presence of VAC extract in hourly intervals. There is a substantial increase of locomotor activity during the administration of the drug combination in column 5 (column 1: 0 mg/kg; column 2: 10 mg/kg; column 3: 25 mg/kg; column 4: 50 mg/kg; column 5: 25 mg/kg+2 mg/kg L-741,626; column 6: L-741,626 4 mg/kg).

EXAMPLES

Example 1

Figure 1:
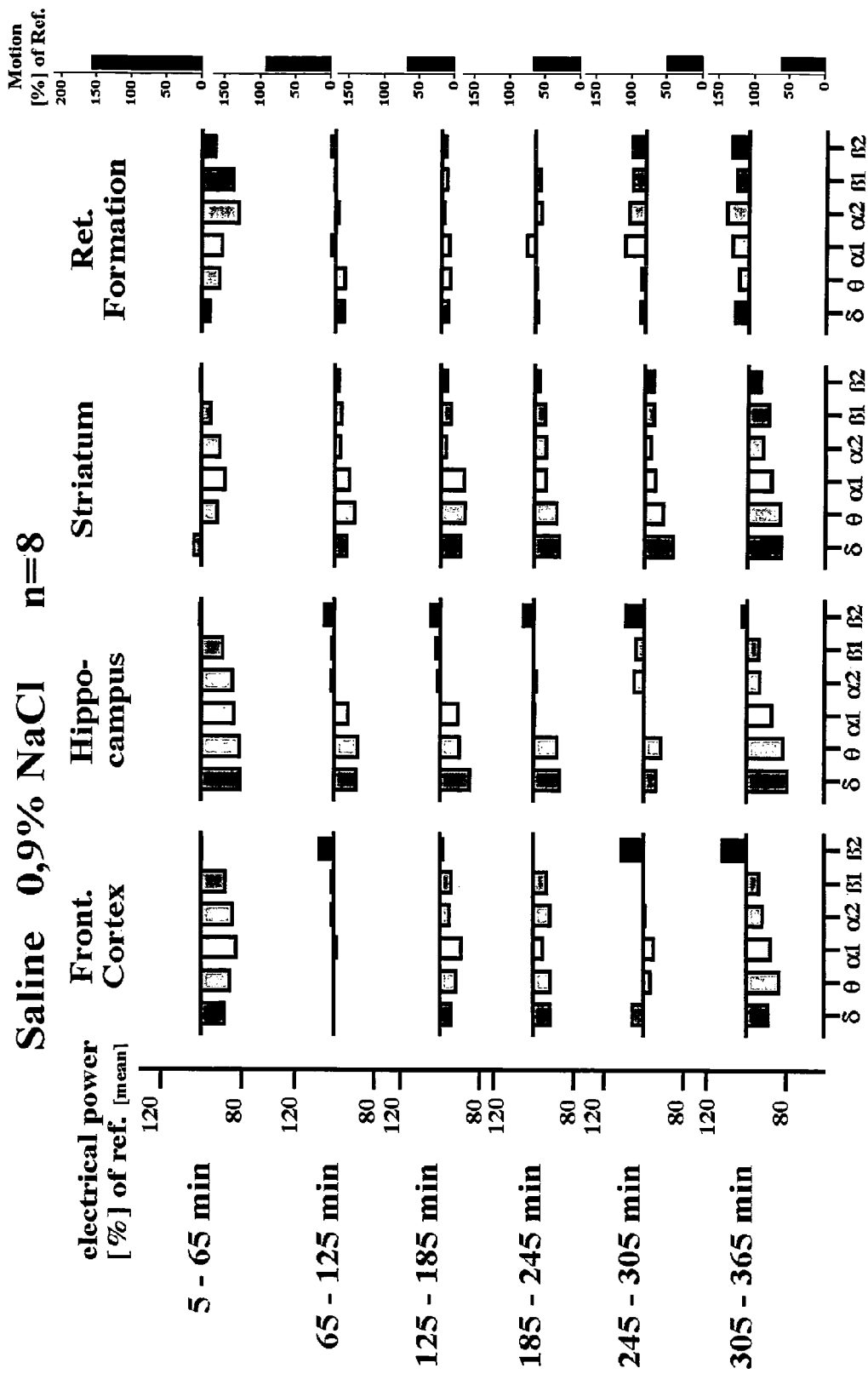

In order to demonstrate that VAC extract Ze 440 of Zeller AG is actually active within the central nervous system (CNS) after oral administration at the D2 receptor as well as the D3 receptor subtypes, experiments in chronically instrumented, freely moving animals were performed. Field potentials were recorded from several brain areas (cortex, hippo-campus, striatum, reticular formation) and, in addition, the locomotor activity was monitored after oral administration of the VAC extract.

Material and Methods

Experimental Procedures

Eight adult Fisher rats (about 6 month of age and day—night converted) were implanted with 4 bipolar concentric steel electrodes within a stereotactic surgical procedure. All four electrodes were placed 3 mm lateral within the left hemisphere. Anterior coordinates are 12.2, 5.7, 9.7 and 3.7 mm for frontal cortex, hippocampus, striatum and reticular formation (according to the atlas of Paxinos and Watson, 1982). A base plate carrying the electrodes (neurological electrodes "SNF 100" from Rhodes Medical Instruments, Inc., Summerland, Calif. 93067, USA) and a 5-pin-plug was fixed to the skull by dental cement attached to 3 steel screws fixed into the skull. The distant recording spot of the electrode was the active electrode whereas the proximal spots of the four electrodes were connected to each other to give a common reference. The base was carrying a plug to receive later on the transmitter (weight: 5.2 g including battery, 26×12×6 mm of size; Rhema Labortechnik, Hofheim, Germany, using 40 Megahertz as carrier frequency).

Experiments were performed in compliance with the German Health Authority Guidelines and with local authority approval. EEG signals were recorded from frontal cortex, hippocampus, striatum and reticular formation and were processed as described previously (Dimpfel et al., Radioelectroencephalography (Tele-Stereo-EEG) in the rat as a pharmacological model to differentiate the central action of flupirtine from that of opiates, diazepam and phenobarbital, Neuropsychobiology, 16: 163-168 (1986)). After automatic artefact rejection, signals were collected in sweeps of 4 s duration and submitted to Fast Fourier Transformation. The resulting electrical power spectra were divided into 6 frequency ranges: delta (0.8-4.5 Hz); theta (4.75-6.75 Hz); alpha1 (7.00-9.50 Hz); alpha2 (9.75-12.50 Hz); beta1 (12.75-18.50 Hz); beta2 (18.75-35.00 Hz). Spectra were averaged in steps of 3 minutes each and displayed on-line. In an off-line procedure spectra were averaged to give 60 minutes for data presentation and further statistical analysis. One oral dose of the total extract diluted in distilled water were investigated using the "Tele-Stereo-EEG" animal model consisting of continuous recording of intra-cerebral field potentials in a group of 8 animals using a crossover design with at least one week of washout period in between the administrations. Control animals consisted of oral administration of 1 ml/kg of a physiological saline solution. After a reference period of 45 minutes for baseline recording (set to 100%), and 5 minutes of adaptation after oral administration of either extract or saline physiological effects were observed continuously for further 360 minutes subdivided into 60 min periods. Changes of electrical power ($\mu V^2/\omega$) are expressed as % of the 45 minutes absolute pre-dose electrical power values within each frequency band. Data was averaged from all animals who gave valuable recordings for the particular experimental day. Multivariate statistics were calculated according to Ahrens and Läuter (Mehrdimensionale Varianzanalyse, Akademie-Verlag, Berlin, 1974). Locomotoric activity was measured by a video tracking system developed by GJB Datentechnik GmbH (D-98704—Langenwiesen, Germany). Mean values±SE/SD and statistics are required, likewise as a TAB. (all dosages and all time points).

The VAC extract Ze 440 was manufactured by means of 60% ethanol. Castiacin was used as the marker substance for the quality control process (Hoberg E, Meier B, Sticher O. 1999. Quantitative high performance liquid chromatographic analysis of diterpenoids in Agni-casti fructus. *Planta Medica* 66: 352-355). The drug extract ratio (DER) was 6-12:1. For the experiments the extract Nr. 39673 (charge: 500400) was used (the content of bicyclic diterpenes was in the range of 2 to 4% by weight). The extract was solved in distilled water and administered by oral gavage.

The specific dopamine receptor D2 antgonist L-741,626 (charge 4* A171544) was purchased from Bio Trend (D-50933—Köln, Germany) and intra-peritoneal (i.p.) injected.

Results—CNS Activity

Figure 2:
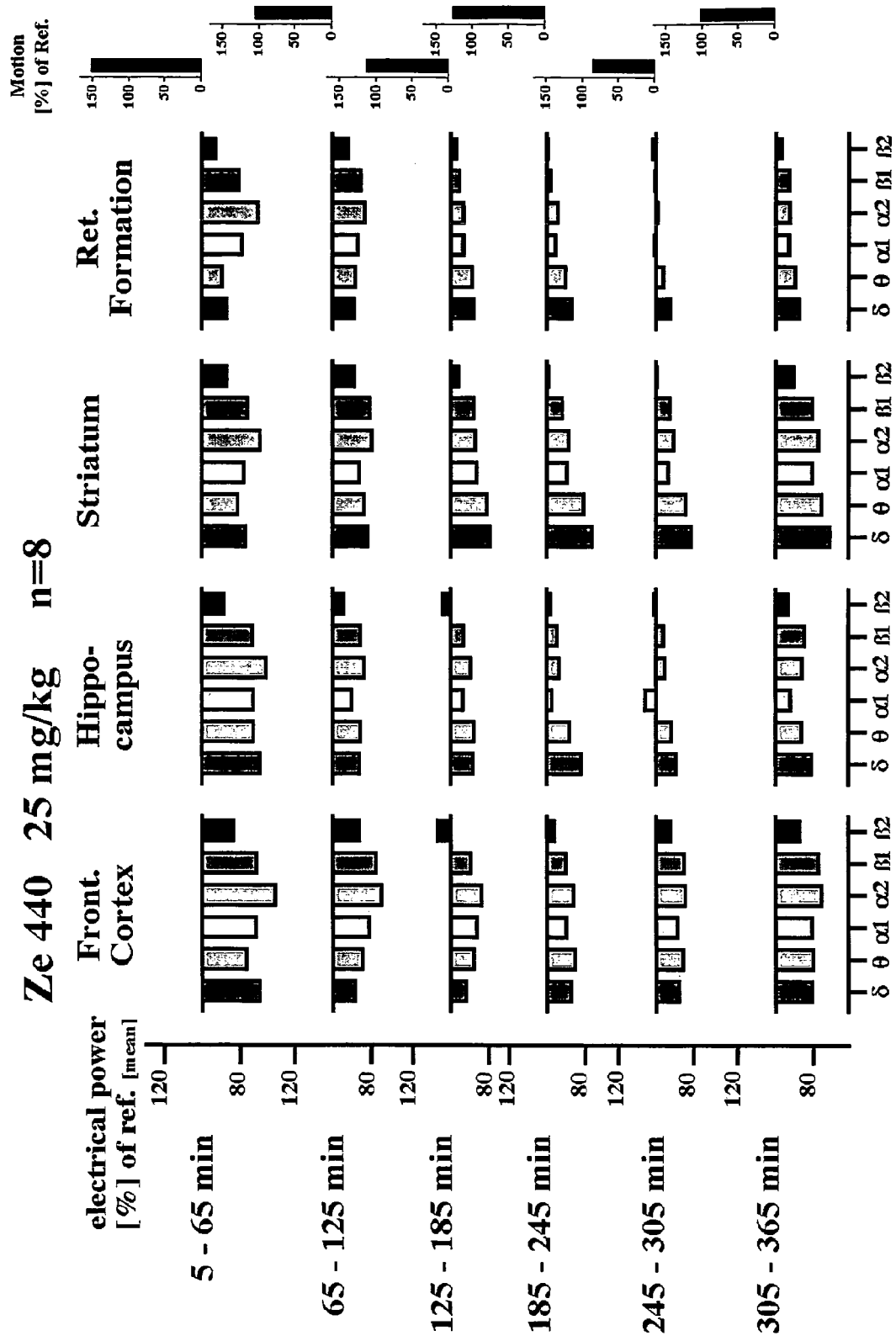

Oral administration of saline did not provide any changes in the EEG power spectrum in comparison of the reference period values except for some weak changes during the first hour after oral administration (FIG. 1). Administration of 10 mg/kg of Ze 440 resulted in changes to alpha2 power within the hippocampus and with the reticular formation (data not shown). Higher dosage (25 mg/kg) provoked a general decrease of spectral power dominated by changes within the alpha2 band, secondly by changes in the delta frequencies (see FIG. 2). These changes were statistically significant with respect to frontal cortex and striatum (see Tables 1 to 6 below). Further increase of the dosage (50 mg/kg) did not create stronger actions rather the other way round. Therefore, the response to Ze 440 is a U-shaped response to.

Figure 3:
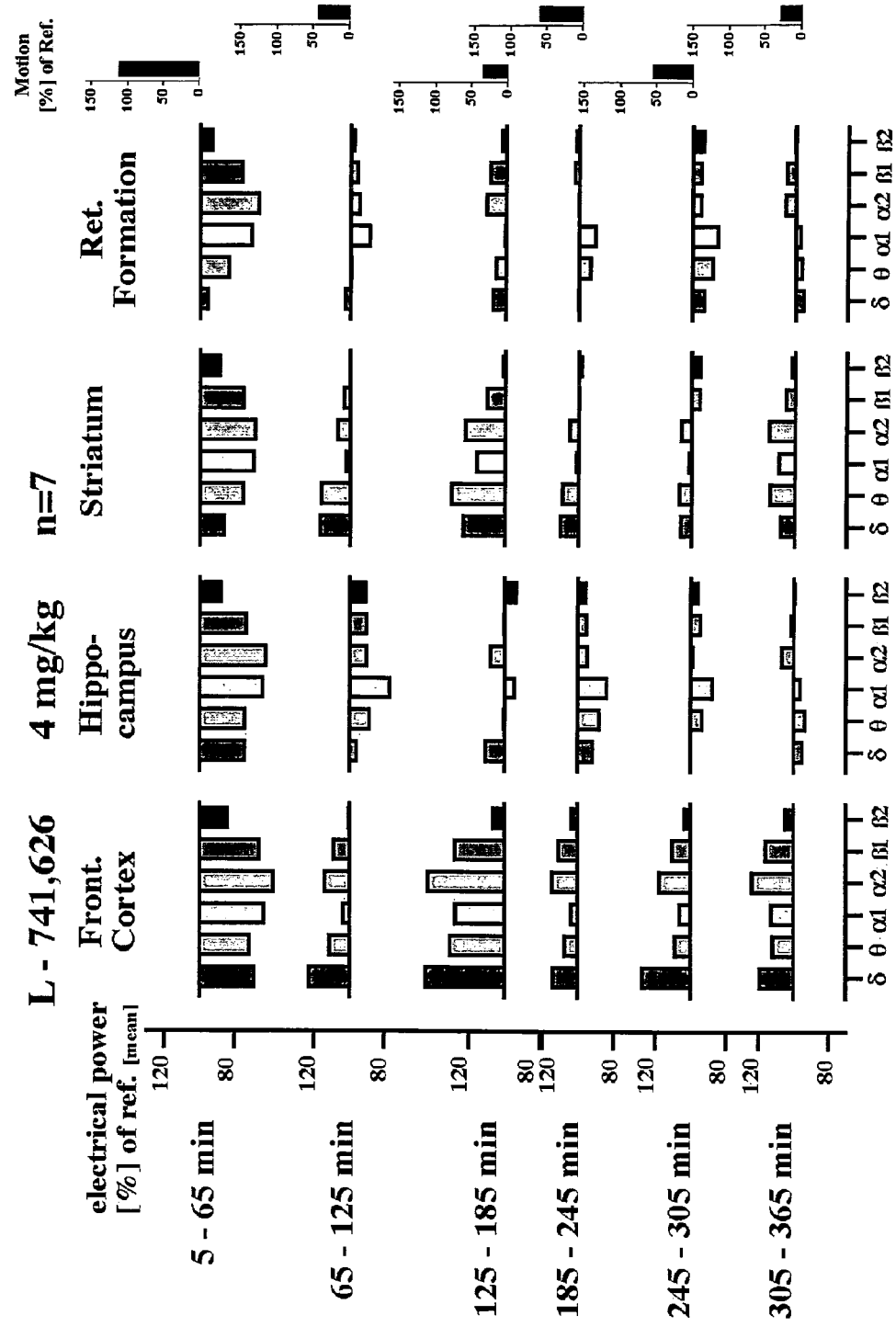
Figure 4:
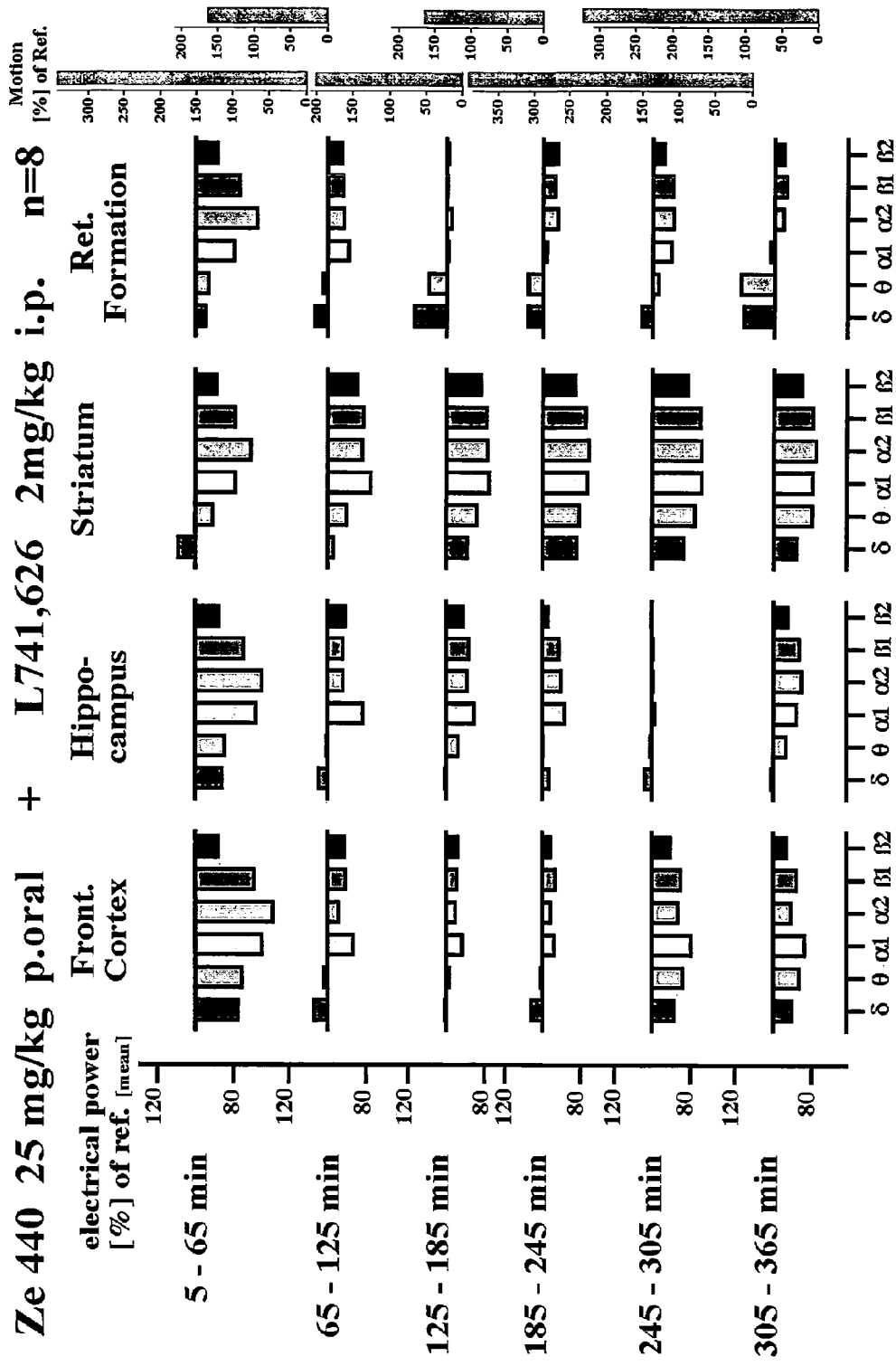
Figure 5:
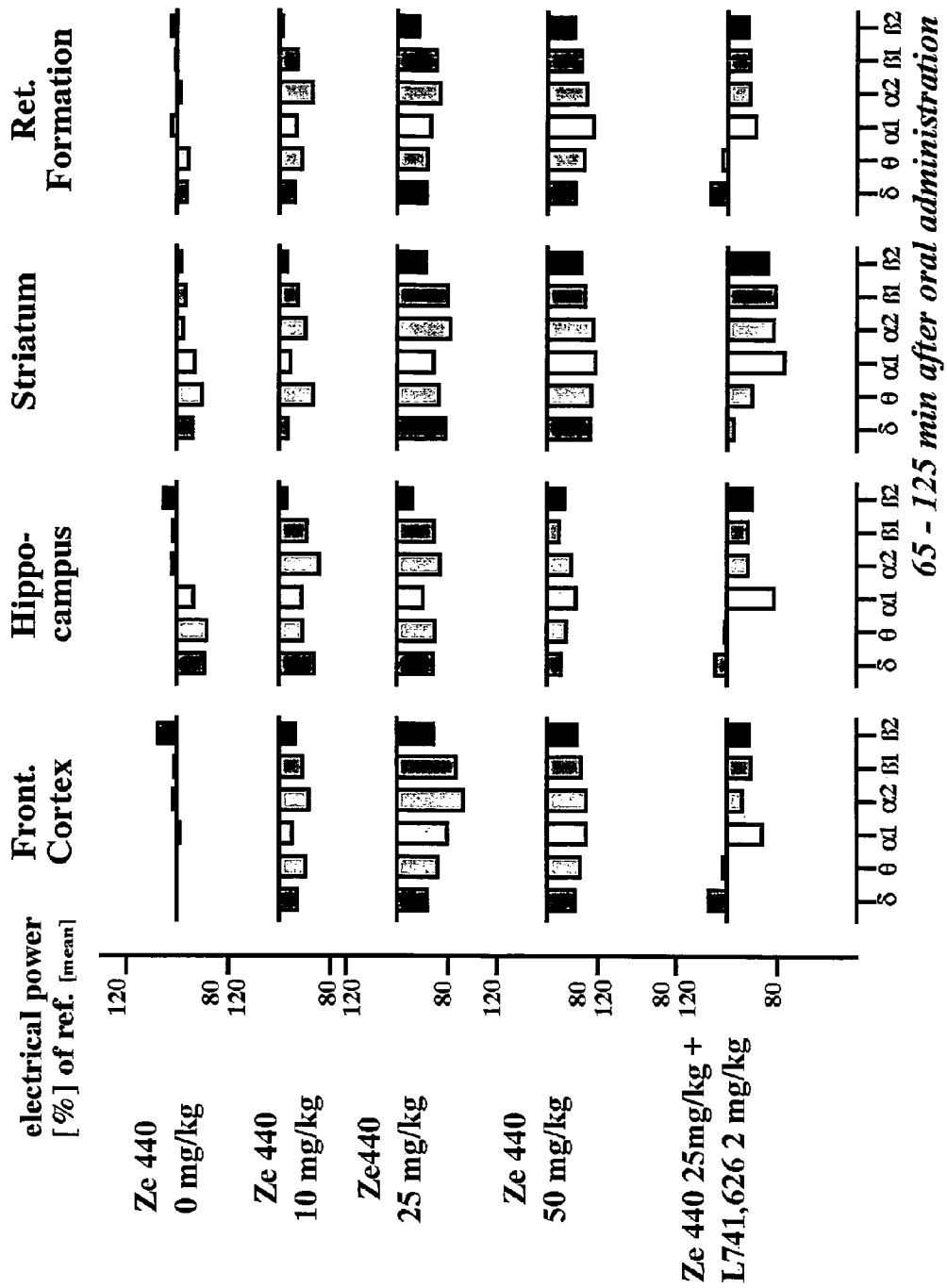
Figure 6:
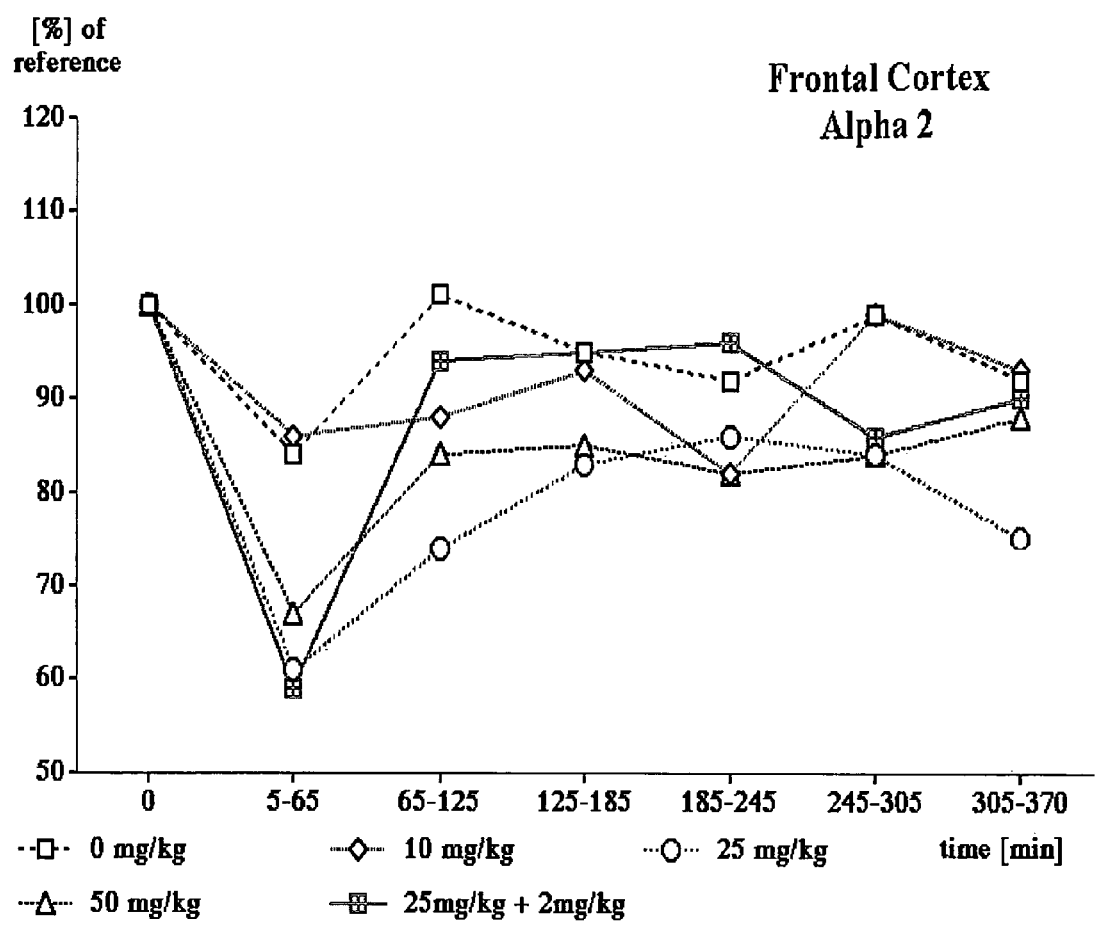
Figure 7:
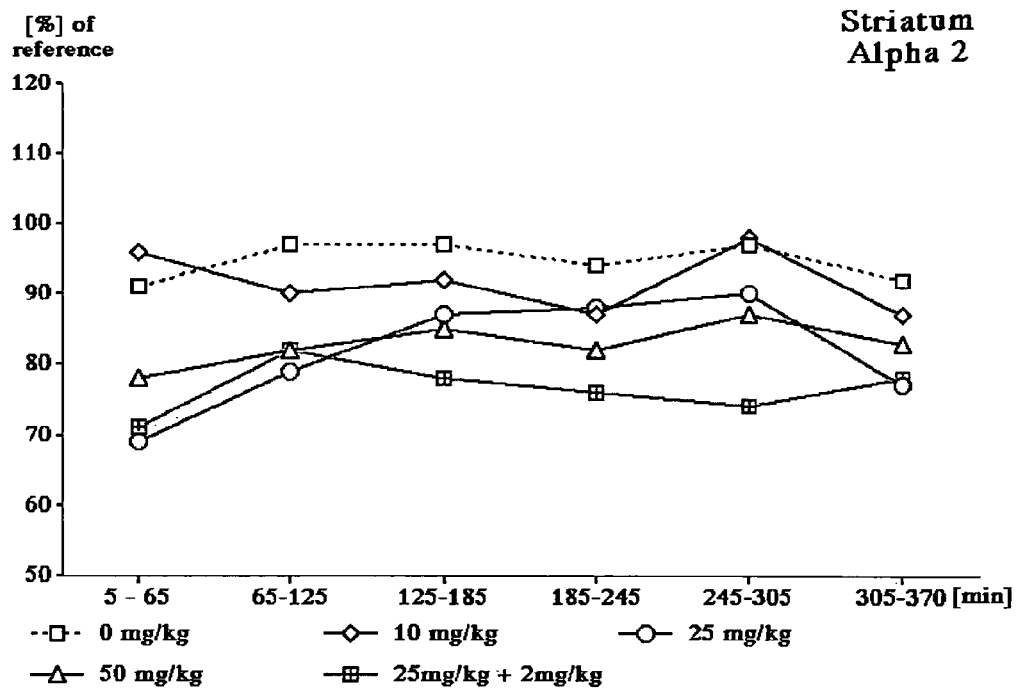
Figure 8:
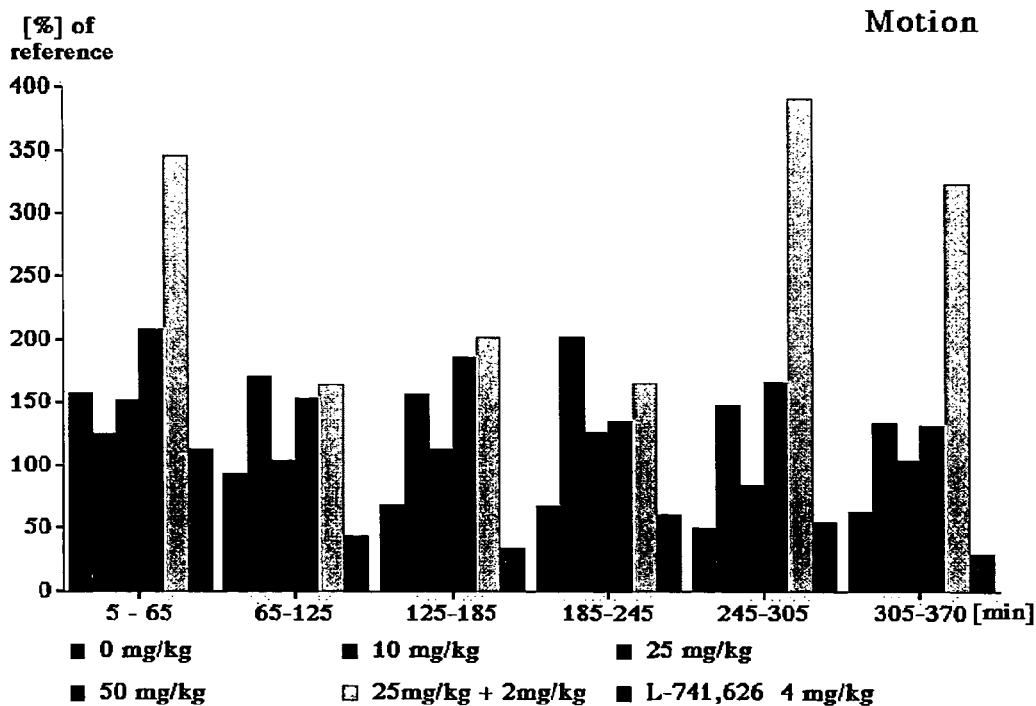

After i.p. administration of 4 mg L-741,626 a strong decrease of spectral power mainly within the alpha2 waves was observed followed by a graduate appearance of increase in alpha 2 and delta waves indicating the blockade (FIG. 3). Oral administration of Ze 440 (25 mg/kg) after i.p. application of 2 mg L—741,626 enforced significantly the alpha2 wave decrease (table 1 below) in the frontal cortex within the first hour. For the following 3 hours (65-245 minutes) the blockade by the antagonist seems to be complete and the action of Ze 440 in the frontal cortex was suppressed. After that total blockade period, some responses in the frontal cortex to Ze 440 re-appeared. In contrast, no blockade could be observed within the striatum (FIG. 4). Therefore, administration of the potent dopamine D2 receptor antagonist discriminates the action of Ze 440 between frontal cortex and striatum.

Results—Locomotor Activity

The locomotor activity of the rats decreased during the observation period (6 hours). After oral administration of Ze 440 (10-50 mg/kg) the locomotors activity did not decrease and remained within the baseline range of the controls for the whole observation period (6 hours). After administration of both, i.e. the antagonist L—741,626 and 25 mg/kg Ze 440 the locomotor activity was twice the baseline value within the first hour of observation. During the following observation period (65-245 minutes) the locomotor activity seemed similar as with pure Ze 440. However, during the later observation period (245-370 minutes) the locomotor activity reached again the value recorded within the first hour. Therefore, the locomotor activity was less expressed only during that time period, where in the frontal cortex the blockade is complete.

The above results demonstrate that orally applied VAC extract Ze 440 induces CNS action as evidenced by changes in the power density of the field potentials. Hence, the active compounds of VAC extract are capable of passing the blood-brain barrier in pharmacologically relevant amounts. The prominent actions occur in the frontal cortex and striatum.

The consistent decrease of the $\alpha_2$ frequency reflects the involvement of dopamine as neurotransmitter (Dimpfel 2007—submitted). This suggestion is not only in line with the regional distribution of D3 receptors in the rat brain (Wallace & Booze, *Identification of D3 and receptors in the rat striatum and nucleus accumbens using* ($\pm$)-*7-Hydroxy-N,N-Di-n-[$^3$H]propyl-2-aminotetralin and carbetapentane*. J. Neurochem. 64: 700-710 (1995); Booze & Wallace, *Dopamine D2 and D3 receptors in the rat striatum and nucleus accumbens: use of 7-OH-DPAT and [$^{125}$I]-iodosulpride*. Synapse 19: 1-13 (1995); Stanwood et al., *Quantitative autoradiographic mapping of rat brain dopamine D3 binding with [$^{125}$]7-OH-PI-PAT: evidence for the presence of D3 receptors on dopaminergic and nondopaminergic cell bodies and terminals*. J. Pharmacol. Exp. Ther. 295: 1223-1231 (2000)) but also with changes in psycho-motor behaviour (Canales & Iversen, *Psychomotor-activating effects mediated by dopamine D2 and D3 receptors in the nucleus accumbens*. Pharmacol. Biochem. Behavior 67: 161-168 (2000)) and regional cerebral blood flow response in primates (Black et al., *A possible substrate for dopamine-related changes in mood and behaviour: prefrontal and limbic effects of a D3-preferring dopamine agonist*. PNAS 99: 17113-17118 (2002)). Administration of a specific dopamine D2 receptor antagonist (Millan et al., *S33084, a novel, potent, selective, and competitive antagonist at dopamine D3-receptors: II. Functional and behavioural profile compared with GR18,231 and L741,626*. J. Pharmacol. Exp. Ther. 293:1063-1073 (2000)) suppressed the Ze 440 action on the power density for a restricted period of time within the frontal cortex (65-245 minutes) but not in the striatum (6 hours). This discrimination action of the dopamine D2 receptor antagonist additionally underlined that the striatum related responses is based on dopamine D3 receptor mediated action.

The locomotor activity in the control animals became less with duration of the experiments. However, in the animals receiving VAC extract Ze 440, the locomotor activity remained in the baseline range. After co-administration of the D2 receptor antagonist within the first hour the locomotor activity was additionally elevated, which may be related by pre-synaptic action of the antagonist by which the transmitter concentration became increased. This is in agreement with the increased alpha2 activity in the frontal cortex within the first hour. Moreover after cessation of the D2 receptor antagonist action in the frontal cortex, the locomotor activity remarkably increased further. Therefore, VAC extract Ze 440 contributes to psychomotor arousal as reflected in enhanced locomotor activity (Canales & Iversen, *Psychomotor-activating effects mediated by dopamine D2 and D3 receptors in the nucleus accumbens*. Pharmacol. Biochem. Behavior 67: 161-168 (2000)).

The above experimental evidence demonstrates that the dopamine D3 receptor mediated action of orally administered VAC extract Ze 440 is active within CNS. This clearly demonstrates bioavailability of the compounds responsible for this action, probably diterpenes and that the target organ is actually contacted. The occurrence of the D3 mediated action of VAC extract in brain is of particular interest since stimulation of dopamine D3 receptors exclusively seems to protect and repair the loss of dopaminergic innervations of the striatum and other basal ganglia which is important for movement disorder.

TABLE 1

Statistical evaluation with respect to single frequency ranges within the four brain areas.

| 5-65 min | mg/kg | n | Delta | Theta | Alpha 1 | Alpha 2 | Beta 1 | Beta 2 |
|---|---|---|---|---|---|---|---|---|
| Frontal Cortex | | | | | | | | |
| Ze 440 | 10.00 | | 0.00 | 0.08 | 0.00 | 0.00 | 0.01 | 0.10 |
| Ze 440 | 25.00 | | 2.59* | 0.74 | 0.83 | 3.00* | 1.82 | 1.72 |
| Ze 440 | 50.00 | | 0.59 | 0.55 | 0.48 | 1.08 | 0.76 | 0.97 |
| Ze 440 + L741,626 | 25 + 2 | | 2.47 | 1.36 | 2.18 | 4.17** | 2.37 | 0.93 |
| Hippocampus | | | | | | | | |
| Ze 440 | 10.00 | | 0.44 | 0.32 | 0.03 | 0.01 | 0.01 | 0.02 |
| Ze 440 | 25.00 | | 0.95 | 0.06 | 0.66 | 2.26 | 1.71 | 1.33 |
| Ze 440 | 50.00 | | 0.03 | 0.04 | 0.17 | 0.53 | 0.56 | 1.23 |
| Ze 440 + L741,626 | 25 + 2 | | 0.16 | 0.32 | 1.25 | 2.28 | 1.33 | 1.52 |
| Striatum | | | | | | | | |
| Ze 440 | 10.00 | | 0.00 | 0.04 | 0.00 | 0.04 | 0.05 | 0.02 |
| Ze 440 | 25.00 | | 3.29* | 0.49 | 0.51 | 2.61* | 2.49 | 1.58 |
| Ze 440 | 50.00 | | 0.77 | 0.23 | 0.27 | 0.60 | 1.00 | 1.11 |
| Ze 440 + L741,626 | 25 + 2 | | 0.08 | 0.10 | 0.52 | 2.15 | 1.66 | 1.27 |
| Ret. Formation | | | | | | | | |
| Ze 440 | 10.00 | | 0.00 | 0.09 | 0.02 | 0.25 | 0.10 | 0.23 |
| Ze 440 | 25.00 | | 0.66 | 0.08 | 0.64 | 0.85 | 0.14 | 0.02 |
| Ze 440 | 50.00 | | 0.11 | 0.21 | 0.71 | 0.46 | 0.35 | 0.23 |
| Ze 440 + L741,626 | 25 + 2 | | 0.08 | 0.10 | 1.04 | 2.26 | 0.66 | 0.34 |

Error probability:
*$p < 10\%$;
**$p < 5\%$.
Multivariate statistics according to Ahrens and Läuter, 1974.
5-65 min

TABLE 2

Statistical evaluation with respect to single frequency ranges within the four brain areas.

| 65-125 min | mg/kg | n | Delta | Theta | Alpha 1 | Alpha 2 | Beta 1 | Beta 2 |
|---|---|---|---|---|---|---|---|---|
| Frontal Cortex | | | | | | | | |
| Ze 440 | 10.00 | 8 | 0.19 | 0.35 | 0.05 | 0.42 | 0.41 | 0.98 |
| Ze 440 | 25.00 | 8 | 0.75 | 1.25 | 1.28 | 2.95* | 3.06* | 2.84* |
| Ze 440 | 50.00 | 8 | 0.72 | 0.85 | 0.87 | 1.13 | 1.13 | 2.26 |
| Ze 440 + L741,626 | 25 + 2 | 8 | 0.13 | 0.17 | 1.35 | 1.17 | 1.13 | 1.75 |
| Hippocampus | | | | | | | | |
| Ze 440 | 10.00 | 8 | 0.02 | 0.02 | 0.02 | 1.14 | 0.82 | 0.59 |
| Ze 440 | 25.00 | 8 | 0.03 | 0.05 | 0.05 | 1.36 | 1.26 | 0.85 |
| Ze 440 | 50.00 | 8 | 0.12 | 0.03 | 0.26 | 0.61 | 0.30 | 1.22 |
| Ze 440 + L741,626 | 25 + 2 | 8 | 0.69 | 0.42 | 0.87 | 0.83 | 0.67 | 2.00 |
| Striatum | | | | | | | | |
| Ze 440 | 10.00 | 8 | 0.05 | 0.03 | 0.00 | 0.16 | 0.08 | 0.02 |
| Ze 440 | 25.00 | 8 | 0.87 | 0.29 | 0.23 | 1.36 | 1.76 | 0.75 |
| Ze 440 | 50.00 | 8 | 0.54 | 0.42 | 0.60 | 0.99 | 1.01 | 1.29 |
| Ze 440 + L741,626 | 25 + 2 | 8 | 0.01 | 0.10 | 1.02 | 1.62 | 1.81 | 1.89 |
| Ret. Formation | | | | | | | | |
| Ze 440 | 10.00 | 8 | 0.03 | 0.12 | 0.27 | 0.59 | 0.29 | 0.08 |
| Ze 440 | 25.00 | 8 | 0.50 | 0.54 | 0.96 | 1.35 | 1.45 | 0.85 |
| Ze 440 | 50.00 | 8 | 0.43 | 0.83 | 2.15 | 1.70 | 1.66 | 1.72 |
| Ze 440 + L741,626 | 25 + 2 | 8 | 0.46 | 0.06 | 1.02 | 0.93 | 0.80 | 0.93 |

Error probability:
*$p < 10\%$;
**$p < 5\%$.
Multivariate statistics according to Ahrens and Läuter, 1974.
65-125 min.

TABLE 3

Statistical evaluation with respect to single frequency ranges within the four brain areas.

| 125-185 min | mg/kg | n | Delta | Theta | Alpha 1 | Alpha 2 | Beta 1 | Beta 2 |
|---|---|---|---|---|---|---|---|---|
| Frontal Cortex | | | | | | | | |
| Ze 440 | 10.00 | 8 | 0.07 | 0.00 | 0.00 | 0.12 | 0.22 | 0.27 |
| Ze 440 | 25.00 | 8 | 0.07 | 0.10 | 0.06 | 0.54 | 0.19 | 0.14 |
| Ze 440 | 50.00 | 8 | 0.56 | 0.47 | 0.26 | 0.70 | 0.58 | 0.90 |
| Ze 440 + L741,626 | 25 + 2 | 8 | 0.00 | 0.00 | 0.02 | 0.21 | 0.10 | 0.23 |
| Hippocampus | | | | | | | | |
| Ze 440 | 10.00 | 8 | 0.04 | 0.00 | 0.19 | 2.25 | 1.81 | 1.86 |
| Ze 440 | 25.00 | 8 | 0.06 | 0.03 | 0.05 | 0.44 | 0.33 | 0.00 |
| Ze 440 | 50.00 | 8 | 0.27 | 0.00 | 0.22 | 0.55 | 0.37 | 1.03 |
| Ze 440 + L741,626 | 25 + 2 | 8 | 0.66 | 0.00 | 0.41 | 0.96 | 1.31 | 2.15 |
| Striatum | | | | | | | | |
| Ze 440 | 10.00 | 8 | 0.15 | 0.07 | 0.00 | 0.34 | 0.45 | 0.26 |
| Ze 440 | 25.00 | 8 | 0.86 | 0.31 | 0.04 | 0.54 | 0.44 | 0.04 |
| Ze 440 | 50.00 | 8 | 0.73 | 0.84 | 0.68 | 1.32 | 1.17 | 1.38 |
| Ze 440 + L741,626 | 25 + 2 | 8 | 0.02 | 0.15 | 0.43 | 1.77 | 1.67 | 1.92 |
| Ret. Formation | | | | | | | | |
| Ze 440 | 10.00 | 8 | 0.00 | 0.20 | 0.18 | 0.81 | 0.43 | 0.02 |
| Ze 440 | 25.00 | 8 | 0.74 | 0.55 | 0.15 | 0.46 | 0.10 | 0.03 |
| Ze 440 | 50.00 | 8 | 0.06 | 0.39 | 0.79 | 1.27 | 0.88 | 0.88 |
| Ze 440 + L741,626 | 25 + 2 | 8 | 0.59 | 0.09 | 0.11 | 0.43 | 0.10 | 0.08 |

Error probability:
*p < 10%;
**p < 5%.
Multivariate statistics according to Ahrens and Läuter, 1974.
125-185 min

TABLE 4

Statistical evaluation with respect to single frequency ranges within the four brain areas.

| 185-245 min | mg/kg | n | Delta | Theta | Alpha 1 | Alpha 2 | Beta 1 | Beta 2 |
|---|---|---|---|---|---|---|---|---|
| Frontal Cortex | | | | | | | | |
| Ze 440 | 10.00 | 8 | 0.06 | 0.34 | 0.45 | 0.72 | 0.93 | 0.77 |
| Ze 440 | 25.00 | 8 | 0.08 | 0.31 | 0.13 | 0.14 | 0.04 | 0.07 |
| Ze 440 | 50.00 | 8 | 0.26 | 0.20 | 0.61 | 0.44 | 0.52 | 1.04 |
| Ze 440 + L741,626 | 25 + 2 | 8 | 0.15 | 0.03 | 0.19 | 0.12 | 0.14 | 0.20 |
| Hippocampus | | | | | | | | |
| Ze 440 | 10.00 | 8 | 0.30 | 0.28 | 1.51 | 4.04** | 2.76* | 2.74* |
| Ze 440 | 25.00 | 8 | 0.06 | 0.00 | 0.02 | 0.05 | 0.06 | 0.37 |
| Ze 440 | 50.00 | 8 | 0.06 | 0.02 | 0.85 | 0.32 | 0.11 | 0.58 |
| Ze 440 + L741,626 | 25 + 2 | 8 | 0.27 | 0.29 | 0.69 | 0.43 | 0.49 | 0.66 |
| Striatum | | | | | | | | |
| Ze 440 | 10.00 | 8 | 0.08 | 0.26 | 0.16 | 0.41 | 0.50 | 0.28 |
| Ze 440 | 25.00 | 8 | 0.88 | 0.52 | 0.11 | 0.23 | 0.10 | 0.00 |
| Ze 440 | 50.00 | 8 | 0.68 | 0.75 | 1.25 | 1.26 | 1.43 | 1.59 |
| Ze 440 + L741,626 | 25 + 2 | 8 | 0.15 | 0.36 | 0.90 | 1.48 | 1.63 | 1.57 |
| Ret. Formation | | | | | | | | |
| Ze 440 | 10.00 | 8 | 0.05 | 0.97 | 1.60 | 1.99 | 0.97 | 0.32 |
| Ze 440 | 25.00 | 8 | 0.78 | 0.53 | 0.33 | 0.06 | 0.00 | 0.02 |
| Ze 440 | 50.00 | 8 | 0.64 | 1.51 | 3.24* | 1.70 | 1.47 | 2.24 |
| Ze 440 + L741,626 | 25 + 2 | 8 | 0.20 | 0.04 | 0.45 | 0.41 | 0.21 | 0.57 |

Error probability:
*p < 10%;
**p < 5%.
Multivariate statistics according to Ahrens and Läuter, 1974.
185-245 min

TABLE 5

Statistical evaluation with respect to single frequency ranges within the four brain areas.

| 245-305 min | mg/kg | n | Delta | Theta | Alpha 1 | Alpha 2 | Beta 1 | Beta 2 |
|---|---|---|---|---|---|---|---|---|
| Frontal Cortex | | | | | | | | |
| Ze 440 | 10.00 | 8 | 0.11 | 0.00 | 0.01 | 0.02 | 0.13 | 0.87 |
| Ze 440 | 25.00 | 8 | 1.22 | 0.66 | 0.20 | 0.90 | 1.05 | 1.70 |
| Ze 440 | 50.00 | 8 | 0.62 | 0.42 | 0.32 | 0.97 | 1.08 | 2.48 |
| Ze 440 + L741,626 | 25 + 2 | 8 | 1.71 | 1.41 | 1.51 | 2.04 | 1.83 | 2.12 |
| Hippocampus | | | | | | | | |
| Ze 440 | 10.00 | 8 | 0.13 | 0.00 | 0.72 | 1.21 | 0.91 | 1.74 |
| Ze 440 | 25.00 | 8 | 0.02 | 0.00 | 0.11 | 0.22 | 0.15 | 0.24 |
| Ze 440 | 50.00 | 8 | 0.17 | 0.16 | 0.29 | 0.14 | 0.03 | 0.65 |
| Ze 440 + L741,626 | 25 + 2 | 8 | 0.15 | 0.04 | 0.39 | 1.18 | 0.93 | 1.71 |
| Striatum | | | | | | | | |
| Ze 440 | 10.00 | 8 | 0.64 | 0.02 | 0.03 | 0.01 | 0.03 | 0.00 |
| Ze 440 | 25.00 | 8 | 0.32 | 0.37 | 0.08 | 0.33 | 0.17 | 0.00 |
| Ze 440 | 50.00 | 8 | 0.49 | 0.78 | 0.94 | 1.17 | 1.27 | 0.81 |
| Ze 440 + L741,626 | 25 + 2 | 8 | 0.02 | 0.94 | 1.58 | 2.70* | 2.55 | 1.92 |
| Ret. Formation | | | | | | | | |
| Ze 440 | 10.00 | 8 | 0.18 | 0.34 | 1.11 | 1.21 | 0.61 | 0.47 |
| Ze 440 | 25.00 | 8 | 0.43 | 0.16 | 0.24 | 0.30 | 0.09 | 0.11 |
| Ze 440 | 50.00 | 8 | 1.40 | 2.70* | 4.91** | 3.45* | 3.02* | 4.03** |
| Ze 440 + L741,626 | 25 + 2 | 8 | 0.11 | 0.13 | 1.44 | 2.36 | 1.22 | 0.78 |

Error probability:
*$p < 10\%$;
**$p < 5\%$.
Multivariate statistics according to Ahrens and Läuter, 1974.
245-305 min

TABLE 6

Statistical evaluation with respect to single frequency ranges within the four brain areas.

| 305-365 min | mg/kg | n | Delta | Theta | Alpha 1 | Alpha 2 | Beta 1 | Beta 2 |
|---|---|---|---|---|---|---|---|---|
| Frontal Cortex | | | | | | | | |
| Ze 440 | 10.00 | 8 | 0.29 | 0.40 | 0.09 | 0.00 | 0.02 | 0.61 |
| Ze 440 | 25.00 | 8 | 0.36 | 0.13 | 0.19 | 1.00 | 1.08 | 1.79 |
| Ze 440 | 50.00 | 8 | 0.04 | 0.05 | 0.00 | 0.13 | 0.14 | 1.24 |
| Ze 440 + L741,626 | 25 + 2 | 8 | 0.12 | 0.14 | 0.51 | 0.90 | 0.87 | 1.36 |
| Hippocampus | | | | | | | | |
| Ze 440 | 10.00 | 8 | 0.00 | 0.00 | 0.25 | 1.09 | 0.84 | 1.48 |
| Ze 440 | 25.00 | 8 | 0.01 | 0.10 | 0.08 | 0.16 | 0.28 | 0.46 |
| Ze 440 | 50.00 | 8 | 0.73 | 0.68 | 0.02 | 0.02 | 0.04 | 0.39 |
| Ze 440 + L741,626 | 25 + 2 | 8 | 0.94 | 0.20 | 0.01 | 1.05 | 0.91 | 1.61 |
| Striatum | | | | | | | | |
| Ze 440 | 10.00 | 8 | 0.55 | 0.00 | 0.00 | 0.11 | 0.03 | 0.02 |
| Ze 440 | 25.00 | 8 | 1.17 | 0.57 | 0.29 | 1.11 | 0.73 | 0.24 |
| Ze 440 | 50.00 | 8 | 1.22 | 0.84 | 0.77 | 1.23 | 0.91 | 0.83 |
| Ze 440 + L741,626 | 25 + 2 | 8 | 0.08 | 0.23 | 0.45 | 1.32 | 0.89 | 0.79 |
| Ret. Formation | | | | | | | | |
| Ze 440 | 10.00 | 8 | 0.62 | 0.98 | 1.31 | 2.10 | 1.00 | 0.87 |
| Ze 440 | 25.00 | 8 | 0.86 | 0.39 | 0.30 | 0.57 | 0.25 | 0.31 |
| Ze 440 | 50.00 | 8 | 1.85 | 3.40* | 3.86** | 3.16* | 2.25 | 3.10* |
| Ze 440 + L741,626 | 25 + 2 | 8 | 0.37 | 0.00 | 0.44 | 1.75 | 0.94 | 0.67 |

Error probability:
*$p < 10\%$;
**$p < 5\%$.
Multivariate statistics according to Ahrens and Läuter, 1974.
305-365 min

Example 2

This example demonstrates the strong binding affinity of various VAC extracts (60% ethanol, v/v) (Ze 440) to human recombinant dopamine D3 receptors ($IC_{50}$ values are approximately 5 µg/ml). The comparison of standardised Ze 440 VAC extracts of eight different batches revealed similar potency of binding inhibition to D3 receptors. In addition to the similar phytochemical profile determined by HPTLC, these results support the dual concept of standardisation combining pharmacological and phytochemical data in order to maintain a constant quality of phytomedicinal drugs. The results further indicate that the dopaminergic action of VAC extracts is also due to dopamine D3 receptors in addition to the earlier proposed D2 receptors.

Experimental Procedures

Human recombinant dopamine D3 receptor was expressed in CHO cells as previously described (Lundstrom & Turpin, *Proposed schizophrenia related gene polymorphism: expression of the Ser9Gly mutant dopamine D3 receptor with the Semliki Forest virus system*, Biochem. Biophys. Res. Commun., 225: 1068-1072 (1996)). Briefly, linearised plasmids of pSFV1-D3 and pSFV-Helper2 were in vitro transcribed and co-electroporated into BHK cells for in vivo packaging of recombinant SFV particles. CHO cells were then infected with activated SFV-D3 viruses and harvested 16 hrs after infection. Membranes were isolated by homogenisation in 50 mM Tris/HCl buffer pH 7.4, 1 mM EDTA and 5 mM $MgCl_2$, and centrifugation at 40'000 g for 15 min. After washing the membranes were stored at −80° C. For binding studies membranes were homogenised in 50 mM Tris/HCl pH 7.4 and 5 µg protein/assay was incubated with $^3$H-7-OH-DPAT (0.1 nM; Amersham) for 1 hr at RT. Non-specific binding was defined in the presence of (+)-butaclamol ($10^{-5}$ M). Binding was terminated by rapid filtration with GF/C filters under reduced pressure and three washes with cold Tris/HCl pH 7.4 buffer. Radioactivity on filters was determined by liquid scintillation counting (TRI-CARB 2100TR, Packard). Relative specific binding was plotted and curve fittings were performed to calculate $IC_{50}$ values.

Figure 9:
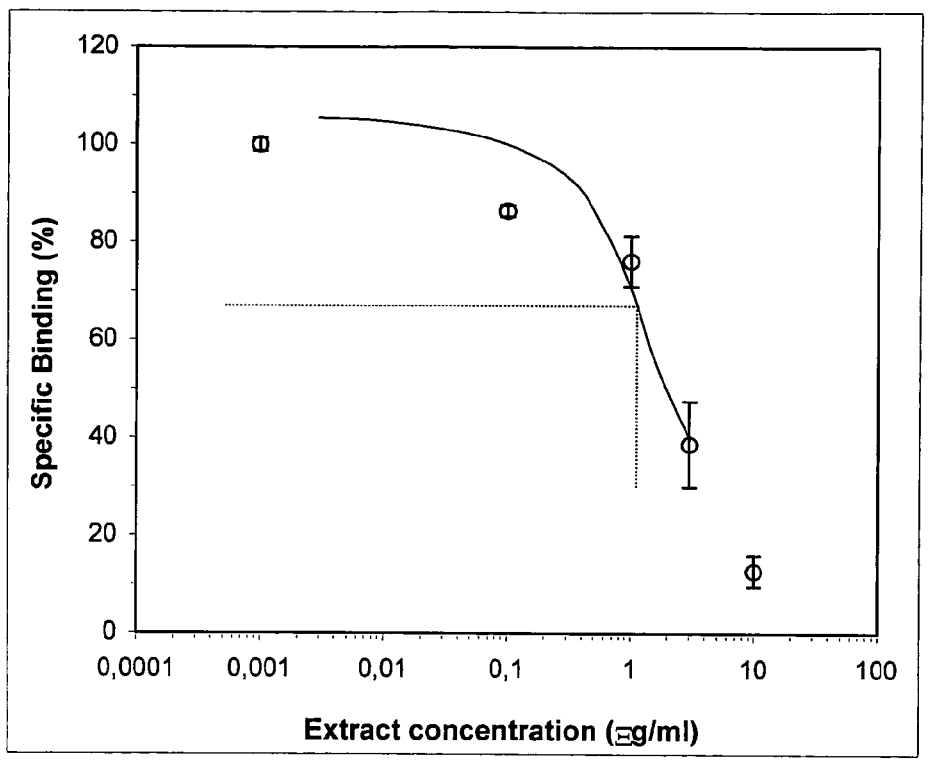
FIG. 9 shows the competitive binding of $^3$H-7-OH-DPAT (7-hydroxy-N,N-di-n-propyl-2-aminotetralin) to human recombinant D3 receptors in the presence of the concentrated VAC extract V 23/95 (=Ze 440). Specific binding is given as mean values±S.E. (n=3).
Figure 10:
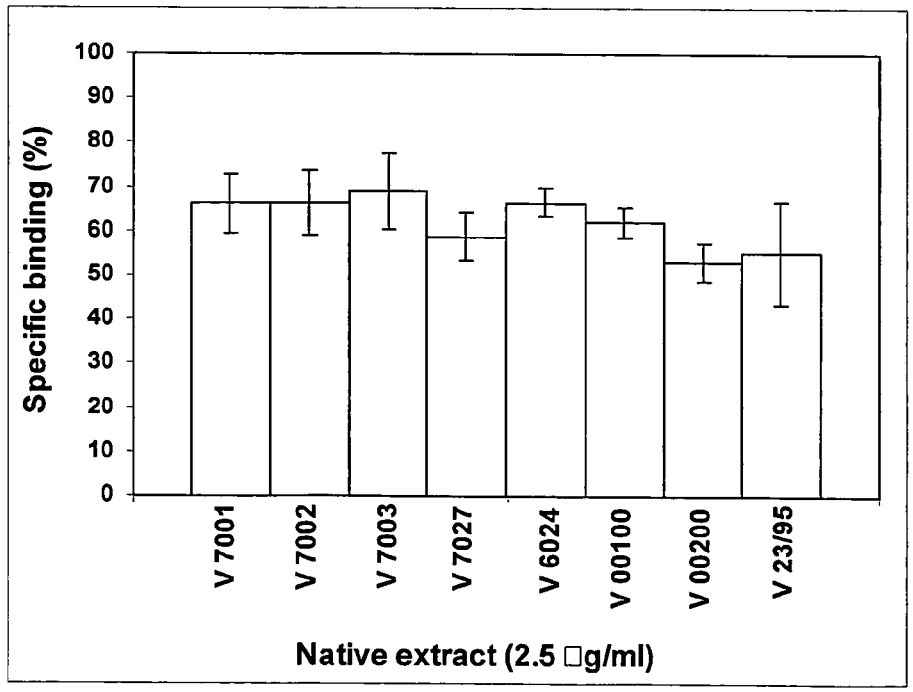
FIG. 10 shows a comparison of VAC extracts of different batches of Ze440 on $^3$H-7-OH-DPAT to human recombinant D3 receptors. Specific binding is given as mean values±S.E.M. of two individual experiments performed in triplicates.

Binding of $^3$H-7-OH-DPAT to human recombinant D3 receptors was inhibited by the concentrated extract V23/95 (Ze 440) with an $IC_{50}$ value of about 3 µg/ml/see FIG. 9). Hence, the potency of the VAC extract to inhibit binding to D3 receptors is >10 times higher than with the binding of $^3$H-spiridone to D2 receptors (Meier et al., *Pharmacological activities of Vitex agnus-castus extracts in vitro*. Phytomedicine 7: 373-381 (2000)). The D3 receptor selectivity is quite high. This D3 receptor binding was used to determine the pharmacological activity of eight Ze 440 extracts of different batches in vitro. All extracts were compared according to their potency to inhibit the binding of $^3$H-7-OH-DPAT to human D3 receptors at a test concentration of 2.5 µg/ml (FIG. 10). All batches inhibited the binding with similar potencies (31-47%) to the D3 receptor indicating constancy of quality in terms of pharmacological activity. Hence, VAC extract has a reproducible and highly specific binding affinity to the dopamine D3 receptor.

Example 3

This example is directed to an observational clinical study on humans for evaluating the efficacy of orally administered VAC extracts for relieving movement disorder symptoms, in this case RLS symptoms, in patients previously treated with dopamine agonists.

Six patients with mild to medium RLS symptoms previously treated with dopamine agonists or L-Dopa received two dosages of 20 mg ZE 440 extract tablets every evening by oral administration. The progression of RLS symptoms was investigated according to the evaluation questionnaire for Restless Leg Syndrome (International RLS severity scale (IRLS)) as set forth in the Leitlinien der Deutschen Gesellschaft für Neurologie; Restless Leg Syndrom ("Guidelines of the German Society of Neurology; Restless Leg Syndrome"). The evaluation of the questionnaires demonstrated that the patients experienced a substantial amelioration of RLS symptoms and did not require conventional synthetic dopamine agonists. The study is still ongoing.

Example 4

This example is directed to a further observational clinical study for evaluating the efficacy of orally administered VAC extracts for relieving RLS symptoms in nine human patients.

Nine patients with mild to medium RLS symptoms received two dosages of 40 mg ZE 440 extract tablets every evening by oral administration. The progression of RLS symptoms was investigated as referenced above. There were no signs of side effects so far. The evaluation of the questionnaires demonstrated that two patients were non-responsive whereas two other patients were mildly responsive (So far the treatment time is rather short and treatment will be continued). The remaining five patients experienced a substantial amelioration of RLS symptoms. Three of the five responsive patients had previously been treated with Restex and the co-administration of Ze 440 allowed for reducing the dosage of Restex substantially (reduction by 50%). Restex is a combination of (i) Levodopa, a prodrug of the transmitter dopamine, dopamine deficiency being a cause for RLS, and (ii) Benserazid, which is added to prevent metabolic decomposition of Levodopa in the blood stream. Typical side effects of Restex/Levodopa and other conventional dopamine agonists are loss of appetite, nausea and restlessness. In addition, Restex/Levodopa and other conventional dopamine agonists are subject to augmentation, i.e. prolonged administration of Restex can actually enhance instead of ameliorate clinical symptoms.

As demonstrated in this study, Ze 440 being a dopamine receptor D2/D3 agonist can not only effectively treat RLS symptoms by itself without side effects but can also be co-administered together with dopamine prodrugs and other conventional dopamine agonists allowing for their dosage reduction, thus leading to reduced side effects and avoiding augmentation. The study is still ongoing.

Example 5

Yawning behaviour in rats is a well-studied phenomenon and known to be regulated by a variety of neurotransmitter systems. Recently, a specific role of the D3 receptor in the induction of yawning behaviour was demonstrated. A series of D3 preferring agonists induced dose-dependent increases of yawning at low doses (Collins et al., Yawning and hypothermia in rats: effects of dopamine D3 and D2 agonists and antagonists. Psychopharmacology 193: 159-170 (2007).

In this experiment the potent binding affinity of ZE 440 to the dopamine D3 receptor in rats was demonstrated by means of the classical yawning test using five dosages of ZE 440 and comparing their effects to saline.

The experiments were performed in accordance with the regulations of the National Act on the Use of Experimental Animals and E.U. guidelines. Animals were naive male Wistar rats (HsdCpb:Wu, Harlan Winckelmann, Borchen) kept under controlled laboratory conditions (light/dark cycle 12:12, lights on at 06.00 a.m., temperature 20±2° C. and air humidity 55-60%). They had free access to commercial rat pellets (Altromin 1326) and tap water. The animals were housed in groups of 5 in Macrolon IV cages. At the beginning of the investigations the rats were 8 weeks old. Five different dosages of ZE440 (6.25, 12.5, 25, 50 and 100 mg/kg body weight) were administered orally. The solutions was freshly prepared. Control animals received saline. Each treatment group had 15 animals.

For the test, animals were placed in separate glass barrels (diameter 16 cm, height 20 cm) mounted on a revolving support 30 min after administration of the substance. Four rats were observed simultaneously. The number of yawns was counted over a period of 90 min starting immediately after placing the animals into the glass barrels, i.e. the observation period lasted from 30 to 120 minutes after administration. Yawning behaviour was defined as a prolonged wide opening of the mouth following by a rapid closure.

Figure 11:
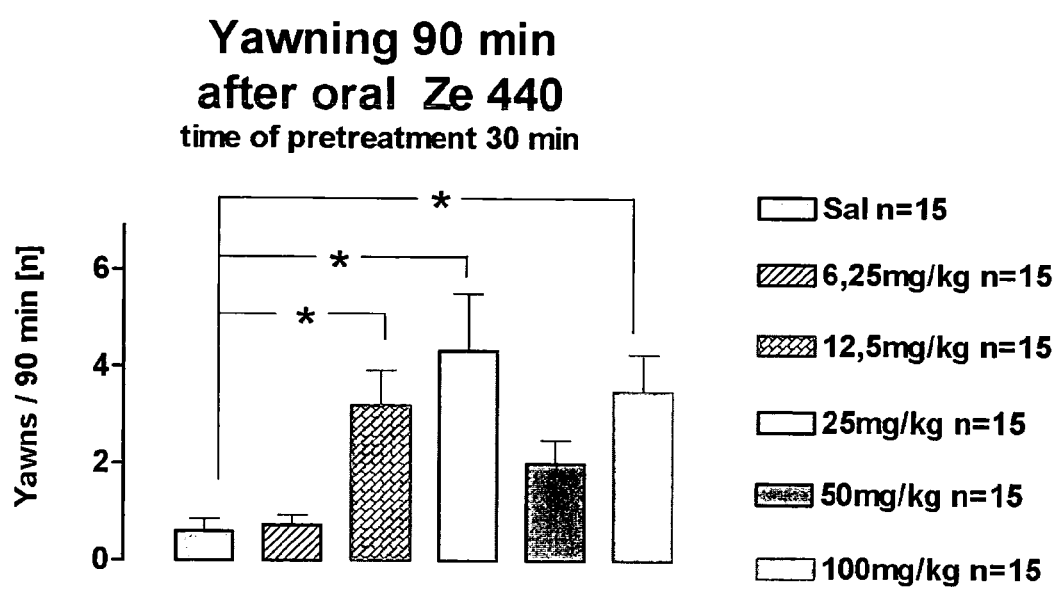
FIG. 11 shows the effect of extract ZE 440 in the yawning test of example 5; ordinate: total number of yawns in 90 min, means±SEM.

The results were analysed using the repeated measures ANOVA followed by post hoc Dunnett-T (two-tailed) using SPSS 13 software for Windows. Only a few yawn reactions were observed in control animals as well as in the group treated with 6.25 mg/kg Ze 440. Significantly enhanced yawning values were observed in groups receiving 12.5 mg/kg, 25 mg/kg and 100 mg/kg Ze 440 (Repeated measures: interval versus treatment F5, 84=2.595 p=0.031; Treatment F5, 84=4.4969, p=0.001; Post-hoc Dunnett-T, two-tailed saline versus 6.25 mg/kg p=1.0; saline versus 12.5 mg/kg p=0.048; saline versus 25 mg/kg p=0.002; saline versus 50 mg/kg p=0.5; Saline versus 100 mg/kg p=0.029). The results are summarized in FIG. 11 below.

The results of the yawning test demonstrate a significant effect of the extract ZE 440 on the yawning behaviour of rats and, thus, prove that extract ZE 440 is bio-available and effectively reaches dopamine D3 receptors in the CNS, where it induces a reaction that is indicative of D3 receptor activation.

The invention claimed is:

1. A method of treating a movement disorder comprising administering to a patient in need thereof a composition comprising an effective amount of an extract from *Vitex agnus castus*; wherein the movement disorder is selected from the group consisting of Restless Leg Syndrome (RLS), and Periodic Limb Movement disorder (PLMD).

2. The method of claim 1, wherein said extract is an aqueous ethanolic extract comprising 40 to 80% ethanol.

3. The method of claim 2, wherein said extract is an aqueous ethanolic extract comprising 50 to 70% ethanol.

4. The method of claim 3, wherein said extract is an aqueous ethanolic extract comprising 60% ethanol.

5. The method of claim 1, wherein said composition comprises extract of *Vitex agnus castus* in the range of 1 to 100 mg extract per dosage form and optionally comprises at least one pharmaceutically compatible excipient.

6. The method of claim 5, wherein said composition comprises extract of *Vitex agnus castus* in the range of 5 to 80 mg per dosage form.

7. The method of claim 6, wherein said composition comprises extract of *Vitex agnus castus* in the range of 10 to 50 mg per dosage form.

8. The method of claim 7, wherein said composition comprises extract of *Vitex agnus castus* in the range of 20 to 40 mg per dosage form.

9. The method of claim 1, wherein the composition is in a dosage form designed for administration as one selected from an oral form, a parenteral form and a transdermal form.

10. The method of claim 9, wherein the oral form is selected from a solution and a tablet.

11. The method of claim 1, wherein the composition further comprises at least one a pharmaceutically compatible dopamine receptor agonist selected from D2 and/or D3 receptor agonist.

12. The method of claim 11, wherein the dopamine receptor agonist is selected from the group consisting of L-dopa, tramadol, paroxetine, metanicotine, piridebil, ropinirole, cabergoline, carbidopa, bromocryptine, domperidone, pergolide, α-dihydroergocryptine, pramipexol, rotigotine and apomorphine.

13. The method of claim 12, wherein the dopamine receptor agonist is pramipexol.

14. A method of treating a movement disorder comprising administering to a patient in need thereof a composition comprising an effective amount of bicyclic diterpenes obtained from *Vitex agnus castus*, wherein the bicyclic diterpenes are selected from the group consisting of cleroda-7,14-dien-13-ol and cleroda-1,3,14-trien-13-ol; and wherein the movement disorder is selected from the group consisting of Restless Leg Syndrome (RLS), and Periodic Limb Movement disorder (PLMD).

* * * * *